United States Patent [19]
Duijsens et al.

[11] Patent Number: 5,942,652
[45] Date of Patent: Aug. 24, 1999

[54] ETHANE PYROLYSIS

[75] Inventors: Emile Maria Joseph Duijsens, The Hague; Pieter Oldenhove, Amsterdam, both of Netherlands

[73] Assignee: Institut Français du Pétrole, France

[21] Appl. No.: 08/935,897

[22] Filed: Sep. 23, 1997

Related U.S. Application Data

[63] Continuation of application No. 08/533,899, Sep. 26, 1995, abandoned.

[30] Foreign Application Priority Data

Sep. 30, 1994 [EP] European Pat. Off. .............. 94202837

[51] Int. Cl.$^6$ ................................. C07C 2/00; C07C 2/02
[52] U.S. Cl. .......................... 585/537; 585/538; 585/539; 585/534
[58] Field of Search .................................... 585/537, 538, 585/539, 534

[56] References Cited

U.S. PATENT DOCUMENTS

| | | | |
|---|---|---|---|
| 2,482,438 | 9/1949 | Robinson | 260/679 |
| 2,645,673 | 7/1953 | Hasche | 260/679 |
| 2,790,838 | 4/1957 | Schrader | 260/679 |
| 3,018,309 | 1/1962 | Krejci | 260/679 |
| 3,116,344 | 12/1963 | Deisler, Jr. | 260/679 |
| 3,153,104 | 10/1964 | Sprauer | 260/679 |
| 3,227,771 | 1/1966 | Happel | 260/679 |
| 3,843,744 | 10/1974 | Kramer et al. | 260/679 R |
| 4,726,913 | 2/1988 | Brophy et al. | 252/373 |
| 4,973,777 | 11/1990 | Alagy et al. | 585/403 |
| 5,242,574 | 9/1993 | Broutin et al. | 208/48 R |

FOREIGN PATENT DOCUMENTS

| | | | |
|---|---|---|---|
| 620174 | 5/1961 | Canada | 585/539 |
| 1169435 | 12/1960 | Germany . | |
| 1335892 | 10/1973 | United Kingdom . | |

OTHER PUBLICATIONS

J. Weill et al., "Production of Olefins and Higher Hydrocarbons by Thermal Coupling of Methane," *Revue de L'Institut Francais du Petrole*, vol. 47, No. 2, pp. 255–267. Mar.–Apr. 1992.

F. Buillaud et al., "Coke Formation During Hydrocarbons Pyrolysis," *Revue de L'Institut Francais Du Petrole*, vol. 48, No. 2, pp. 115–125, Mar.–Apr. 1993.

Foreign Search Report of Jan. 3, 1996.

*Primary Examiner*—Glenn Caldarola
*Assistant Examiner*—Thuan D. Dang
*Attorney, Agent, or Firm*—Millen, White, Zelano & Branigan, P.C.

[57] ABSTRACT

The invention relates to the process for preparing ethyne by the pyrolysis of ethane by heating the same for a period of time that is less than 0.5 sec in a pyrolysis reactor at a temperature in the range of 950 to 1500° C., using steam as diluent gas in a steam/ethane molar ratio of at most 3.

13 Claims, No Drawings

ETHANE PYROLYSIS

This application is a continuation, of application Ser. No. 08/533,899, filed Sep. 26, 1995 now abandoned.

FIELD OF THE INVENTION

The invention relates to the process for the preparation of ethyne by the pyrolysis of ethane.

BACKGROUND TO THE INVENTION

The concept of ethane pyrolysis to produce ethyne is known. In British Patent No. 1,335,892 a process for the preparation of ethyne by pyrolysis of ethane is disclosed comprising heating for a period of time that is less than 0.1 sec. for instance, 0.07 sec, a pre-heated mixture of ethane and steam in a weight ratio of 1:2–3 at a temperature between 1000 and 1100° C, in a tubular reactor having an internal diameter of at most 5 cm. According to this document, the internal diameter must not exceed 5 cm, because the desired temperature will otherwise not be attained whereas the claimed weight ratio of ethane to steam is essential to limit coke formation. During the pre-heating of the mixture, steam should be present because of this coke formation. The example illustrates the preparation of ethyne in a yield of 13.5% wt (on the total effluent after drying).

In U.S. Pat. No. 3,116,344 a process for the preparation of ethyne by pyrolysis of ethane is disclosed of excellent ethyne selectivity through the pyrolysis of a pre-heated mixture in the absence of oxygen or oxygenated dissociation products (e.g., steam) using a vortex tube reactor. However, the mass balance does not mention the amount of coke and it will be realized (in view of the teaching of British patent No. 1,335,892) that coke formation (being a sink of feedstock and a pollutant of the reactor) will be substantial. Example II (best) illustrates the preparation of ethyne in a yield of 50.1% wt (on the total effluent), however, not corrected for the formation of coke.

Thus, although the conditions favoring the formation of ethyne by pyrolysis of ethane are known, heating the same for a period of time less than 0.5 sec at a temperature of say 950 to 1500° C., it remains desirable to produce ethyne in still higher selectivity and yield, i.e., avoiding the formation of coke.

SUMMARY OF THE INVENTION

A process is now provided whereby ethyne can be produced in high selectivity and high yield by pyrolysis of ethane. Thus, the invention provides a process for the preparation of ethyne by the pyrolysis of ethane by heating the same for a period of time that is less than 0.5 sec in a pyrolysis reactor at a temperature in the range of 950 to 1500° C., using steam as diluent gas, wherein steam is used in a steam/ethane molar ratio of at most 3.

The reaction is preferably carried out at a temperature in the range of 1000 to 1200° C. Above 1000° C. the selectivity towards ethyne is sufficiently high to be of commercial interest, whereas below 1500° C. the reaction may still be easily managed. The total residence time in the pyrolysis reactor (including time spent in pre-heating zones thereof, if any) is preferably in the range of 0.05 to 0.3 sec, more preferably in the range of 0.1 to 0.25 sec and most preferably in the range of 0.15 to 0.2 sec.

DETAILED DESCRIPTION OF THE INVENTION

The reaction is preferably carried out in a pyrolysis reactor having a ceramic reaction zone. Silicon carbide is known to reduce the coke formation in the pyrolysis reactor and is therefore the preferred choice of ceramic material. Moreover, the pyrolysis reactor is preferably provided with a cascade of heating zones to bring the mixture of steam/ethane to the desired temperature without having to pre-heat (and prematurely convert) the ethane separately. A pyrolysis reactor having been found to fulfill these conditions, is the pyrolysis reactor disclosed in U.S. Pat. No. 4,973,777. This pyrolysis reactor has a ceramic reaction zone comprising a series of juxtaposed channels grouped in rows and covering at least a part of the length of said reaction zone, parallel to its axis, said channel rows being non adjacent to one another, the reaction zone also comprising on one hand a heating zone surrounding said channel rows either on said part of the reaction zone or on a part of the length of said reaction zone when said channels cover the whole length of the reaction zone, and, on the other hand, a cooling zone following said heating zone.

It is observed that the pyrolysis reactor disclosed in U.S. Pat. No. 4,973,777 is used for the conversion of methane into hydrocarbons with higher molecular weights. Albeit that the use of steam as diluent gas is provided for, e.g., at a steam/methane weight ratio ranging from 1:1 to 10:1, the beneficial presence thereof is neither acknowledged nor illustrated. Moreover, the results achieved using methane as feedstock are quite discouraging. Only partial conversion of methane is reached (50%), while producing mainly ethene (15 mol; 420 g). The selectivity towards ethyne (162.5 g or 8.3% wt on the total effluent including unconverted hydrogen gas and methane) is but comparable to that of benzene (117 g) and that of the liquid phase other than benzene (104 g). Furthermore, as it is known that in the pyrolysis of methane, ethane is formed as an intermediate product (cf., Revue de l'institute Francais du Pétrol, 1993, vol. 48, pp. 115–125), one would expect the same results changing from methane to ethane as a feedstock. It is quite surprising to find the better results by the process according to the present invention.

Besides ethane, the present feedstock may contain ethene in any molar ratio, as ethene is similarly converted into ethyne. However, for economic considerations (ethene is a valuable product usually stripped from the $C_2$ fraction) the feedstock will normally contain no more than 5 mol %, generally about 1.5 mole or less ethene. The feedstock may contain minor amounts of other hydrocarbons without influencing the efficiency and selectivity of the process, say up to 1 mol %. Preferably, the feedstock is composed of pure ethane.

The steam/ethane molar ratio is preferably in the range of 1.5 to 2.5. Contrary to the teaching of the aforementioned British Patent No. 1,335,892, coke formation in the claimed steam/ethane molar ratio is still very low, whereas, surprisingly, the selectivity to ethyne is positively influenced by the presence of steam in the claimed molar ratio. This finding is indeed in clear contrast to what would be expected on the basis of the teaching of U.S. Pat. No. 3,116,344.

EXAMPLES

The invention is illustrated by the following examples.
Equipment

An electrically heated pyrolysis reactor as disclosed in U.S. Pat. No. 4,973,777, operating at 12 kw, with a maximum flow rate of 10 $Nm^3$ per hour and provided with three heating zones lined with silicon carbide was used.
Feedstock Ethane was used containing approximately 1.5 mol % ethene, corresponding to ethane produced in an ethene/ethane splitter of a lower olefins plant.

EXAMPLES 1 AND 2, AND COMPARATIVE EXAMPLE A

All 4 experiments were carried out using a flow rate of 4.2 Nm$^3$ per hour and a total residence time of 0.1 sec. Examples 1 and 2 used steam as diluent (molar ratio of 2) at increasing temperatures. Comparative example A was carried out using nitrogen as diluent gas. The results and process conditions are set out in Table 1. Example 2, at a reaction temperature of 1002° C., provides the highest ethyne/ethene ratio. Although Comparative example A was carried out at a temperature exceeding that of Examples 1 or 2, its ethyne/ethene ratio is the lowest.

EXAMPLES 3 AND 4

Both experiments were carried out using steam (molar ratio of 2) as diluent gas, at a reaction temperature of 986° C. Examples 3 and 4 differ in flow rate and total residence time; a flow rate of 4.2 Nm$^3$ per hour, respectively 2.2 Nm$^3$ per hour and a total residence time of 0.1 sec, respectively 0.16 sec. Comparison reveals a preference for the somewhat longer total residence time. The results and process conditions are set out in Table 2.

EXAMPLES 5 AND 6, AND COMPARATIVE EXAMPLE B

All 3 experiments were carried out using a flow rate of 2.2 Nm$^3$ per hour and a total residence time of 0.16 sec. Examples 5 and 6 used steam as diluent gas, whereas in Comparative example B nitrogen was used (molar ratio of 2). The results and process conditions are set out in Table 3. Comparison of Example 5 and Comparative example B illustrates that a higher ethyne/ethene ratio is achieved using steam as diluent gas. The beneficial temperature effect is illustrated by Example 6.

TABLE 1

| Experiment No. | 1 | 2 | A |
| --- | --- | --- | --- |
| Temp. in heating zone 1 (°C.) | 701 | 704 | 736 |
| Temp. in heating zone 2 (°C.) | 911 | 914 | 930 |
| Temp. in heating zone 3 (°C.) | 993 | 1002 | 1012 |
| Mol ratio nitrogen/ethane | — | — | 2 |
| Mol ratio steam/ethane | 2 | 2 | — |
| Flow rate (Nm$^3$ per hour) | 4.2 | 4.2 | 4.2 |
| Total residence time (sec) | 0.1 | 0.1 | 0.1 |
| Product ratio's (on ethene) | | | |
| propyne, propadiene | <0.01 | <0.01 | <0.01 |
| methane | 0.36 | 0.39 | 0.38 |
| ethyne | 0.37 | 0.43 | 0.33 |
| benzene | 0.03 | 0.03 | 0.03 |
| 1,3-butadiene | 0.02 | 0.02 | 0.01 |
| carbon monoxide | 0.11 | 0.16 | — |
| carbon dioxide | 0.01 | 0.01 | — |
| Conversion (%) | 98.7 | 99.5 | 97.7 |

TABLE 2

| Experiment No. | 3 | 4 |
| --- | --- | --- |
| Temp. in heating zone 1 (°C.) | 707 | 675 |
| Temp. in heating zone 2 (°C.) | 910 | 822 |
| Temp. in heating zone 3 (°C.) | 986 | 986 |
| Mol ratio nitrogen/ethane | — | — |
| Mol ratio steam/ethane | 2 | 2 |
| Flow rate (Nm$^3$ per hour) | 4.2 | 2.2 |
| Total residence time (sec) | 0.1 | 0.16 |
| Product ratio's (on ethene) | | |
| propyne, propadiene | <0.01 | 0.01 |
| methane | 0.34 | 0.44 |
| ethyne | 0.28 | 0.59 |
| benzene | 0.03 | 0.04 |
| 1,3-butadiene | 0.02 | 0.01 |
| carbon monoxide | 0.25 | 0.07 |
| carbon dioxide | 0.02 | <0.01 |
| Conversion (%) | 98.3 | 99.3 |

TABLE 3

| Experiment No. | 5 | 6 | B |
| --- | --- | --- | --- |
| Temp. in heating zone 1 (°C.) | 707 | 745 | 707 |
| Temp. in heating zone 2 (°C.) | 856 | 903 | 839 |
| Temp. in heating zone 3 (°C.) | 1014 | 1069 | 1014 |
| Mol ratio nitrogen/ethane | — | — | 2 |
| Mol ratio steam/ethane | 2 | 2 | — |
| Flow rate (Nm$^3$ per hour) | 2.2 | 2.2 | 2.2 |
| Total residence time (sec) | 0.16 | 0.16 | 0.16 |
| Product ratio's (on ethene) | | | |
| propyne, propadiene | 0.1 | 0.02 | 0.01 |
| methane | 0.58 | 0.98 | 0.57 |
| ethyne | 0.83 | 1.73 | 0.73 |
| benzene | 0..05 | 0.11 | 0.06 |
| 1,3-butadiene | 0.01 | 0.01 | 0.01 |
| carbon monoxide | 0.24 | 0.56 | — |
| carbon dioxide | 0.02 | 0.03 | — |
| Conversion (%) | 99.7 | 99.9 | 99.4 |

We claim:

1. A process of pyrolyzing ethane to produce ethyne comprising heating the ethane for a period of time within a range of 0.05 to 0.3 sec in a pyrolysis reactor having a final heating zone at a temperature in the range of 950 to 1500° C., using steam as diluent gas, wherein the steam is used in a steam/ethane molar ratio of at most 3, the pyrolysis reactor being provided with a cascade of heating zones having progressively increasing temperatures in the direction of flow, and the pyrolysis reactor having a ceramic reaction zone comprising a series of juxtaposed channels grouped in rows and covering at least a part of the length of said reaction zone, parallel to its axis, the channel rows being non adjacent to one another, the reaction zone also comprising a heating zone surrounding the channel rows either on said part of the reaction zone or on a part of the length of the reaction zone when the channels cover the whole length of the reaction zone, and a cooling zone following said heating zone wherein the steam is present in a molar ratio positively influencing selectivity to ethyne production, said heating being conducted substantially solely by indirect heat exchange against surfaces of said channels in said ceramic reaction zone, and wherein said heating is conducted so that preheating to less than 950° C. occurs in heating zones upstream of said final heating zone.

2. The process of claim 1 wherein the reaction is carried out at a temperature in the range of 1000 to 1200° C.

3. The process of claim 1 wherein the residence time in the pyrolysis reactor is within a range of 0.1 to 0.25 sec.

4. The process of claim 1 wherein the residence time in the pyrolysis reactor is within a range of 0.15 to 0.2 sec.

5. The process of claim 1 wherein the ceramic material is silicon carbide.

6. The process of claims 1 wherein ethane containing ethene in a molar ratio of no more than 5 mol % is used.

7. The process of claims 1 wherein ethane containing ethene in a molar ratio of about 1.5 mol % or less is used.

8. The process of claim 1 wherein the steam/ethane molar ratio is in the range of 1.5 to 2.5.

9. A process according to claim 1, wherein the steam/ethane molar ratio is at least about 1.5.

10. The process of claim 1, wherein the steam/ethane molar ratio is at least about 2.

11. The process of claim 1, wherein said cascade of heating zones consists of three heating zones.

12. A process according to claim 11, wherein the temperature in the first heating zone is 745° C., in the second zone 903° C., and in the third heating zone 1069° C., the mole ratio of steam to ethane being 2, and the total residence times being 0.16 seconds, thereby resulting in a conversion of 99.9%.

13. A process according to claim 1, wherein the ethane is heated solely by electrical energy.

* * * * *